United States Patent [19]

Supernaw et al.

[11] Patent Number: 4,990,773
[45] Date of Patent: Feb. 5, 1991

[54] METHOD FOR DETERMINING THE PRODUCIBILITY OF A HYDROCARBON FORMATION

[75] Inventors: Irwin R. Supernaw; Dipak C. Kothari, both of Houston, Tex.

[73] Assignee: Texaco Inc., White Plains, N.Y.

[21] Appl. No.: 278,316

[22] Filed: Dec. 1, 1988

[51] Int. Cl.$^5$ ...................... G01N 21/64; G01N 21/62
[52] U.S. Cl. ........................................ 250/255; 436/31
[58] Field of Search ........................... 250/255; 436/31

[56] References Cited

U.S. PATENT DOCUMENTS

| | | | |
|---|---|---|---|
| Re. 22,081 | 4/1942 | Campbell | 250/255 |
| 2,311,151 | 2/1943 | Campbell | 250/252.1 |
| 2,337,465 | 12/1943 | Heigl | 250/255 |
| 2,367,664 | 1/1945 | Cambell et al. | 250/255 |
| 2,403,631 | 7/1946 | Brown | 250/255 |
| 2,459,512 | 1/1949 | Fash et al. | 250/301 |
| 2,591,737 | 4/1952 | Souther | 250/255 |
| 2,951,940 | 9/1960 | Graham et al. | 250/254 |
| 3,149,068 | 9/1964 | Biederman et al. | 250/255 |
| 3,205,353 | 9/1965 | Bray | 250/43.5 |
| 3,254,959 | 6/1966 | Fallgatter et al. | 250/255 |
| 3,300,641 | 1/1967 | Heinze | 250/254 |
| 3,887,331 | 6/1975 | Baldwin | 436/31 |
| 4,031,398 | 6/1977 | Callis et al. | 250/328 |
| 4,248,599 | 2/1981 | Mommessin | 23/230 HC |
| 4,609,821 | 9/1986 | Summers | 250/255 |
| 4,696,903 | 9/1987 | Owen | 436/28 |
| 4,814,614 | 3/1989 | Tsui | 250/255 |

FOREIGN PATENT DOCUMENTS 8502015  5/1985  United Kingdom ............... 250/255

OTHER PUBLICATIONS

Gordon, Arnold J. and Ford, Richard A., *The Chemist's Companion*, John Wiley & Sons, New York, 1972, pp. 167 and 168.
Speight et al., On the Molecular Nature of Petroleum Asphaltenes, American Chemical Society, Washington D.C. 1981, pp. 1-15.
Chisholm, B. R., Eldering, H. G. et al., Total Luminescene Contour Spectra of Six Topped Oils, BETC/RI-76/16, (Nov. 1966), Prepared for ERDA in Bartlesville Energy Center.
Brownrigg, J. T. et al., Low Temperature Total Luminescence Contour Spectra of Six Topped Oils and Their Vacuum Distillate and Residuum Fractions, BETC RI-78/13, Prepared for DOE for the Bartlesville Energy Technology Center. Hemphill, W. R. et al., Laboratory Analysis and Airborne Detection of Materials Stimulated to Luminesce by the Sun, Journal of Luminescence, vol. 31 and 32, pp. 724-726, North-Holland Amsterdam (1984).
Skoog, Douglas, *Principles of Instrumental Analysis*, Sauders College Publishing, Philadelphia, (3rd ed. 1985), pp. 225-240.

Primary Examiner—Constantine Hannaher
Assistant Examiner—Jacob Eisenberg
Attorney, Agent, or Firm—Jack H. Park; Kenneth R. Priem; Harold J. Delhommer

[57] ABSTRACT

The invention is a method of evaluating a sample of an underground formation such as drill cuttings to determine the producibility of any hydrocarbons present in the formation by solvating a sample in a polar solvent which will solvate asphaltenes, solvating the sample in an aliphatic solvent which will solvate most crude fractions without solvating asphaltenes, quantitatively measuring the emission fluorescence at a wavelength below 400 nm of both solvated samples at an excitation wavelength at which most petroleum compounds fluoresce, and determining the producibility of any hydrocarbon present in the sample by comparing the emission fluorescence of the two samples to previous correlations made between fluorescence and known producibility.

10 Claims, No Drawings

METHOD FOR DETERMINING THE PRODUCIBILITY OF A HYDROCARBON FORMATION

BACKGROUND OF THE INVENTION

This invention is related to techniques for evaluating the hydrocarbon content and composition of an underground formation. More particularly, the invention offers a method for determining from samples such as drill cuttings whether the asphaltene content of a hydrocarbon formation is high enough to cause the formation to be non-producible.

Because of the difficulties and cost involved in producing highly viscous oils, it is frequently desirable to know the producibility of a hydrocarbon formation without placing a well on test. This is particularly true in geographical areas such as California which have a relatively high percentage of viscous hydrocarbons. Current logging techniques are often ineffective in evaluating the producibility of an underground formation prior to placing a well on test.

In some situations, electric logs do not effectively differentiate between hydrocarbons and water, and rarely between non-producible and producible oil. Even though electric logs may correctly identify the presence of pore-filling carbonaceous material, they are unaffected by the viscosity of the oil which is a significant factor in determining whether oil will flow into the wellbore.

Mud log data is commonly used instead of wireline log data in an attempt to evaluate a formation prior to an expensive DST (Drill Stem Test) or putting a well on production test. The mud logs leave a great deal to be desired as an accurate indicator of the presence of petroleum, and if present, of productive formations.

Fluorescence has been used as a logging technique for detecting oil in drill cuttings for decades. However, the method used to determine the fluorescence of samples at a rig site is a crude method which has not improved appreciably and is severely limited in its usefulness and applicability. At present, fluorescence is determined when an operator shines a broad spectrum ultraviolet light source on cuttings in the hope of seeing substantial fluorescence to indicate the presence of oil. See U.S. Pat. Nos. 2,311,151; 2,337,465; 2,459,512; 2,951,940 and Re. No. 22,081.

There are several inherent problems in current fluorescence logging which make it nonquantitative at best and misleading at worst. First, the excitation source is not concentrated in the spectral region where the oil is most likely to absorb radiation and re-emit that radiation as fluorescence. Second, the oil is quite likely to emit fluorescence at wavelengths predominantly, if not totally, unseen by the human eye. Third, the fluorescence observed by the operator is influenced by the presence of fluorescent minerals such as fluorite. Fourth, the presence or amount of oil on the surface of the cuttings samples may not be representative of the oil in the pore structure of the formation. The mud logger sees only the surface of the samples with this technique. Fifth, operators' description of such fluorescence phenomena is highly subjective. Such commonly used words as strong, weak, bright, dull, yellow, and gold prohibit any quantitative analysis of the data.

U.S. Pat. No. 4,696,903 discloses shining UV light on formation samples and visually noting the color of the fluorescence as well as taking video pictures of the fluorescence for later study. U.S. Pat. No. 4,248,599 discloses a process for determining the API gravity of oil by the use of a flame ionization detector. In this method, the volatile and pyrolyzable components of oil are vaporized. A measurement is made of the ratio of the amount of hydrocarbon vapor produced at temperatures within a selected high temperature range to the total amount of vapor produced. A ratio of fluorescence measured under two conditions is taken in conjunction with the use of the flame ionization detector.

The emission fluorescence of crude oil samples has been studied and recorded over various wavelengths, including ultraviolet wavelengths below 400 nm. Studies which have taken place at the Bartlesville Energy Technology Center have been basically "fingerprint" studies wherein the emission fluorescence of various types of crude oils has been recorded at different excitation wavelengths. This Department of Energy research was a spin-off from earlier efforts by the Bureau of Mines to try to identify crude oil by emission fluorescence for purposes of pollution control. Please see Chisholm, B. R., Eldering, H. G., Giering, L. P., and Hornig, A. W., Total Luminescence Contour Spectra of Six Topped Crude Oils, BETC/RI-76/16, a paper prepared for ERDA for the Bartlesville Energy Research Center in Bartlesville, Okla., November 1976; and Brownrigg, J. T. and Hornig, A. W., Low Temperature Total Luminescence Contour Spectra of Six Topped Crude Oils and their Vacuum Distillate and Residuum Fractions, BETC/RI-78/13, a paper prepared for DOE for the Bartlesville Energy Technology Center, Bartlesville, Okla., July 1978. Similar, non-published fingerprinting work of crude oils by total luminescence spectra has also been performed in unpublished work at Texas A. & M. University.

There is one recently developed process which employs fluorescent measurement to test for the presence of hydrocarbons within drill cuttings. But this process does not give an indication of viscosity or producibility. Further, U.S. Pat. No. 4,609,821 is applicable only to oil base mud drill cuttings. The cuttings are excited with a wide range of UV wavelengths and the emitted radiation is recorded over a wide range of wavelengths to produce an analytical chemical profile. This profile of intensity over multiple wavelengths of excitation and emission radiation is compared with previous profiles to determine the presence of hydrocarbons not associated with the oil base mud.

Molecular fluorescence is discussed in general in Skoog, Douglas, *Principles of Instrumental Analysis*, Sanders College Publishing, Philadelphia (3rd ed. 1985), pp. 225–240. The reference indicates that the greatest fluorescence behavior occurs with compounds containing aromatic functional groups and offers a table which indicates the UV fluorescence wavelengths associated with numerous benzene derivatives in ethanol solution. Several analytical profiles of hydrocarbons are disclosed wherein fluorescence intensity is plotted over multiple excitation and emission wavelengths.

SUMMARY OF THE INVENTION

The invention is a method of evaluating a sample of an underground formation such as drill cuttings to determine the producibility of any hydrocarbons present in the formation. This decision of producibility is based upon the hydrocarbon asphaltene content, which is usually determinative of whether the hydrocarbon that is present is producible or non-producible.

The method comprises the steps of solvating a sample in a polar solvent which will solvate all petroleum fractions including asphaltenes, solvating a volume of the sample in an aliphatic solvent which will solvate most fractions of crude such as paraffinics, naphthenics and aromatics without substantially solvating asphaltenes, quantitatively measuring the emission fluorescence at a wavelength below 400 nm of both solvated samples at an excitation wavelength at which most petroleum compounds fluoresce, and determining the producibility of any hydrocarbon present in the sample by comparing the emission fluorescence of the two samples to previous correlations made between fluorescence and known producibility. The excitation and emission wavelength bands are preferably fixed and narrow to yield a single fluorescence intensity measurement.

By calculating the ratio of the emission fluorescence of said polar solvent sample to said aliphatic solvent sample and comparing that ratio to previous correlations made with samples of known producibility, the producibility of hydrocarbons that are present can be determined. Alternately, the fluorescence influence of the asphaltenes and associated producibility can be isolated by taking the difference in emission fluorescence between the fluorescence of said polar sample and the fluorescence of said aliphatic solvent sample and comparing that difference to previous correlations.

DETAILED DESCRIPTION

Fluorescence is a phenomena wherein compounds, containing molecular arrangements generally referred to as chromophores, emit fluorescent radiation when excited by incoming light of certain wavelengths. The chromophores contained in compounds such as the asphaltenic, aromatic and resin fractions of crude, fluoresce in the UV portion of the electromagnetic spectrum when bombarded with radiation of the proper excitation wavelength.

Generally, asphaltenes have high levels of chromophores and high levels of fluorescence. Paraffinic and naphthenic fractions of crude have relatively low levels of chromophores, and associated low levels of fluorescence.

A technique known as total scanning fluorescence or 3-D fluorescence has been developed, wherein a sample is excited over a range of discrete wavelengths and the emitted radiation is recorded at various wavelengths. Total scanning fluorescence has indicated that the optimum excitation and emission wavelengths for most crude oils fall below 400 nm. This is a region where the human eye has no response. The optimum excitation wavelengths for most crude oils are in the region of about 250 to about 310 nm. The predominant portion of emitted radiation falls in the non-visible ultraviolet region of about 250 to about 400 nm.

By using a scale of fluorescence intensity and instrumentally measuring the fluorescence of a formation sample from a core or drill cuttings, with and without the presence of substantial asphaltenes, we have discovered that we can determine whether or not a formation crude is producible without putting a well on test. In general, quantitative fluorometer readings are obtained which are related to the amount of asphaltenes in the hydrocarbon being checked. A high asphaltene content makes the oil too viscous to be produced. Thus, the asphaltene content of hydrocarbon is usually determinative of whether or not hydrocarbons are producible.

For the present invention, the determination of whether an oil is producible or non-producible is based on the hydrocarbon asphaltene content. Of course, the formation may contain hydrocarbons with a very high API gravity, but an insufficient volume or saturation of hydrocarbons to be producible. Thus, we assume that the formation samples being checked with the invention contain a sufficient volume of hydrocarbons to be recoverable, and that there are no porosity or permeability problems which would prevent a formation from being produced. "Producibility" when used herein, means that the asphaltene content and related viscosity, is insufficient to create a problem in producing the hydrocarbons. Conversely, an invention determination that hydrocarbons are non-producible means that the asphaltene content is too high for the hydrocarbons to be produced by usual recovery methods. The use of some thermal methods such as steam and hot solvent injection will, of course, change what is producible, and what is non-producible.

As detailed below, we have developed two related methods of evaluating formation samples such as drill cuttings to determine the producibility of any hydrocarbons present in the formation. Both methods involve measuring the fluorescence of the sample in two solvents, a first solvent which will substantially solvate asphaltenes, and a second solvent which will solvate most crude oil fractions without substantially solvating asphaltenes.

The first and preferred method calculates the ratio of the fluorescence of the polar solvent sample to the aliphatic solvent sample and compares that ratio to previous correlations developed between known producibility and said fluorescence ratios. The second method takes the difference between the fluorescence of the two solvated samples and compares that to previous correlations drawn between known producibility and the differences in sample fluorescence. Other methods with different mathematical relationships may also be used, provided that the method in some way isolates the fluorescence due to asphaltenes as do the above ratio and difference methods.

Both methods require that a sample be solvated in two environments, a polar solvent which will solvate asphaltenes and an aliphatic solvent which will solvate most of the fractions of crude oil without substantially solvating asphaltenes. To improve accuracy, a known volume of sample should be solvated in a known volume of solvent In addition, the solvents employed should preferably be the same solvents that were used to develop the previous correlations.

The emission fluorescence is preferably measured instrumentally at a fixed, narrow, emission wavelength below about 400 nm. This quantitative measurement for both solvated samples occurs preferably from a fixed, narrow excitation wavelength at which most petroleum compounds fluoresce. The difference or ratio of the measured emission fluorescence of the two samples is then calculated to yield a value which is proportional to producibility. By comparing the ratio of the emission fluorescence of the polar solvent sample to that of the aliphatic solvent sample, or the difference in emission fluorescence between the two samples to previous correlations, the producibility of the crude may be determined. The difference method is believed to be less sensitive to asphaltene content and producibility than the ratio method. Consequently, the ratio method is preferred.

Preferably, a single fluorescence intensity measurement is obtained for each sample rather than multiple intensity measurements at multiple excitation wavelengths. However, since different crude components and minerals fluoresce at different wavelengths, it may be desirable to obtain multiple intensity measurements of one sample at different wavelengths in order to decrease the influence of a particular component in the drill cuttings.

We have discovered that when the instant ratio is less than three, the hydrocarbons involved are most likely producible. When the ratio is greater than five, the hydrocarbons are most likely non-producible, except under substantial thermal or solvent stimulation. When the ratio is between three and five, the hydrocarbons may or may not be producible as defined herein. It is believed that this correlation will not vary significantly with different crudes.

Both the ratio and the difference method of isolating fluorescence due to asphaltenes give excellent results. If the measured fluorescence intensities of the two samples are relatively close together, the asphaltene content of the sample will be low, and will not be a significant factor in determining producibility. The invention method has greater precision if the asphaltene content of the crude is substantial enough to affect producibility of the formation. With a high asphaltene content there will be a substantial difference between the fluorescence values of the two samples.

Preferred polar solvents for solvating all the fractions of crude including asphaltenic are methylene chloride, chloroform and dichloroethane. Preferred aliphatic solvents for solvating most of the crude fractions without solvating asphaltenes are hexane, heptane, and pentane. The straight chain isomers are most preferred. Other solvents, of course, may be employed.

The following examples will further illustrate the novel method of determining producibility of hydrocarbons from formation samples by the present invention. These examples are given by way of illustration and not as limitations on the scope of the invention. Thus, it should be understood that the steps of the invention method may be varied to achieve similar results within the scope of the invention.

EXAMPLES 1-4

Drill cuttings from four different formations known to contain hydrocarbons were analyzed using the invention method in Examples 1-4. A Sequoia Turner Model 112 fluorometer was employed to determine the producibility of the formations from which the samples came. The Turner Model 112 fluorometer consists basically of an ultraviolet light source, an excitation radiation filter between the light source and the sample, a photomultiplier tube which reads the intensity of radiation emitted by the sample at right angles to the excitation radiation, and an emission filter placed between the sample and the photomultiplier tube. A reference light path between the light source and the photomultiplier is also provided so that the difference between emitted radiation and exciting radiation can be easily determined.

The light source employed for these examples was a far ultraviolet source U tube having Turner Model No. 110-851, GE No. G4T4/1 or equivalent. 95% of the radiation from this light source is at 254 nm, with some output at 297, 313, 405, 436 and 546 nm.

The excitation radiation filter employed was a Turner No. 7-54 filter which has a bell-shaped radiation transmission curve. This filter transmits about 80% of the radiation which strikes it from about 290 to about 360 nm, and 40% or more of incident radiation from about 250 nm to about 390 nm. Only 10% of incident radiation is transmitted at 236 nm and 400 nm. The end result of this combination of light source and excitation radiation filter is that 99% of the excitation radiation used in Examples 1-4 was at 254 nm.

The emission filter employed was a 320 nm narrow band filter. The transmission curve of this emission filter allows 25% transittance of incident radiation at 320 nm, dropping steeply to 20% transmittance at 313 nm and 327 nm. Transmittance is only 4% at 310 nn and 330 nm.

The invention method is by no means limited to the combination of filters and light source employed with the Turner Model 112 fluorometer. Other fluorometers, light sources including lasers, and filters may be employed with the invention method with equal success. What the invention requires is that the solvated samples be radiated at an excitation wavelength at which most petroleum compounds fluoresce, generally below about 400 nm, and preferably about 250 nm to about 310 nm. The emission fluorescence must be measured below about 400 nm, preferably within the region of about 250 nm to about 400 nm. Although these examples were run with an excitation radiation of 254 nm and emission radiation measured at 320 nm, it may be desirable to change the wavelengths employed to better eliminate the effect of fluorescence from other components present in the drill cuttings, such as minerals, pipe dope, or filtrate of oil base muds.

As indicated in Table 1, the solvents employed for Examples 1-4 were hexane and methylene chloride ($CH_2Cl_2$). The ratios of the methylene chloride to hexane fluorescence for Examples 1 and 2 were 0.8 and 2.85, respectively. Both of these ratios are below 3, and it was predicted from drill cuttings that the formations would be producible. The formations from which the drill cuttings came were indeed producible formations.

On the other hand, Examples 3 and 4 with methylene chloride/hexane ratios of 4.7 and 277, respectively were predicted to be non-producible. In the field, these formations were determined to be non-producible.

TABLE 1

| Ex. No. | Fluorometer Reading Hexane | Fluorometer Reading $CH_2Cl_2$ | Ratio $CH_2Cl_2$ / Hexane | Prediction and Result |
|---|---|---|---|---|
| 1 | 9800 | 7680 | 0.8 | Producible |
| 2 | 516 | 1470 | 2.85 | Producible |
| 3 | 2.2 | 10.3 | 4.7 | Non-Producible |
| 4 | 11 | 3050 | 277 | Non-Producible |

Many other variations and modifications may be made in the concepts described by those skilled in the art without departing from the concepts of the present invention. Accordingly, it should be clearly understood that the concepts disclosed in the description are illustrative only and are not intended as limitations on the scope of the invention.

What is claimed is:

1. A method of evaluating a sample of an underground formation to determine the producibility of any hydrocarbons present in the formation, which comprises:

solvating a known volume of sample in a known volume of a polar solvent which will solvate asphaltenes;

solvating a known volume of said sample in a known volume of an aliphatic solvent which will solvate paraffinics and naphthenics found in underground hydrocarbons without substantially solvating asphaltenes, said sample volume equal to polar solvent sample volume, said aliphatic solvent volume equal to polar solvent volume;

quantitatively measuring the emission fluorescence below about 400 nm of both solvated samples at an excitation wavelength at which most petroleum compounds fluoresce; and determining the producibility of any hydrocarbon present in the sample by calculating the ratio of the emission fluorescence of said polar solvent sample to said aliphatic solvent sample and comparing said ratio to previous correlations drawn from known samples, said previous correlations drawn between known producibility of samples and the ratios of the emission fluorescence of the known samples in said polar solvent to the emission fluorescence of the known samples in said aliphatic solvent.

2. The method of claim 1, wherein the hydrocarbons are producible if said ratio is less than three.

3. The method of claim 1, wherein the hydrocarbons are non-producible if said ratio is greater than five.

4. The method of claim 1, wherein the polar solvent is methylene chloride, chloroform, or 1,1-dichloroethane.

5. The method of claim 1, wherein the aliphatic solvent is hexane, heptane, or pentane.

6. The method of claim 1, wherein the samples are drill cuttings.

7. The method of claim 1, wherein the emission fluorescence is measured between about 250 and about 400 nm.

8. The method of claim 1, wherein the solvated samples are excited between about 250 and about 310 nm.

9. A method of evaluating a sample of an underground formation to determine the producibility of any hydrocarbons present in the formation, which comprises: polar solvent sample volume, said aliphatic solvent volume equal to polar solvent volume;

quantitatively measuring the emission fluoroscence at a fixed wavelength below about 400 nm of both solvated samples at a fixed excitation wavelength at which most petroleum compounds fluoresce; and determining the producibility of any hydrocarbon present in the sample by taking the ratio of the emission fluorescence of said polar solvent sample to said aliphatic solvent sample and comparing said ratio to previous correlations drawn from known samples, said previous correlations indicating that if said ratio is greater than five, the formation hydrocarbons are non-producible, and if said ratio is less than three, the formation hydrocarbons are producible.

10. A method of evaluating a sample of an underground formation to determine the producibility of any hydrocarbons present in the formation, which comprises:

solvating a known volume of sample in a known volume of a polar solvent which will solvate asphaltenes;

solvating a known volume of said sample in a known volume of an aliphatic solvent which will solvate paraffinics and naphthenics found in underground hydrocarbons without substantially solvating asphaltenes, said sample volume equal to polar solvent sample volume, said aliphatic solvent volume equal to polar solvent volume;

quantitatively measuring the emission fluorescence below about 400 nm of both solvated samples at an excitation wavelength at which most petroleum compounds fluoresce; and determining the producibility of any hydrocarbon present by comparing the difference in emission fluorescence between the fluorescence of said polar solvent sample and the fluorescence of said aliphatic solvent sample to previous correlations, said previous correlations drawn between known producibility of samples and the differences of emission fluorescence observed for each of the known samples between the fluoresence of the samples in said polar solvent and in said aliphatic solvent.

* * * * *

UNITED STATES PATENT AND TRADEMARK OFFICE
CERTIFICATE OF CORRECTION

PATENT NO. : 4,990,773

DATED : February 5, 1991

INVENTOR(S) : Irwin Ray Supernaw and Dipak Chhabildas Kothari

It is certified that error appears in the above-identified patent and that said Letters Patent is hereby corrected as shown below:

Claim 9, Cols. 7 and 8, delete "Claim 9" and substitute the correct Claim 9.

--A method of evaluating a sample of an underground formation to determine the producibility of any hydrocarbons present in the formation, which comprises:

solvating a known volume of sample in a known volume of a polar solvent which will solvate asphaltenes;

solvating a known volume of said sample in a known volume of an aliphatic solvent which will solvate paraffinics and naphthenics found in underground hydrocarbons without substantially solvating asphaltenes, said sample volume equal to polar solvent sample volume, said aliphatic solvent volume equal to polar solvent volume;

quantitatively measuring the emission fluorescence at a fixed wavelength below about 400 nm of both solvated samples at a fixed excitation wavelength at which most petroleum compounds fluoresce; and determining the producibility of any hydrocarbon present in the sample by taking the ratio of the emission fluorescence of said polar solvent sample to said aliphatic solvent sample and comparing said ratio to previous correlations drawn from known samples,

UNITED STATES PATENT AND TRADEMARK OFFICE
CERTIFICATE OF CORRECTION

PATENT NO. : 4,990,773

DATED : February 5, 1991

INVENTOR(S) : Irwin Ray Supernaw, et al

It is certified that error appears in the above-identified patent and that said Letters Patent is hereby corrected as shown below:

said previous correlations indicating that if said ratio is greater than five, the formation hydrocarbons are non-producible, and if said ratio is less than three, the formation hydrocarbons are producible.--

Signed and Sealed this

Eighteenth Day of August, 1992

Attest:

DOUGLAS B. COMER

*Attesting Officer*  *Acting Commissioner of Patents and Trademarks*